US011103679B2

United States Patent
Eversull et al.

(10) Patent No.: US 11,103,679 B2
(45) Date of Patent: Aug. 31, 2021

(54) STEERABLE CATHETERS AND METHODS FOR MAKING THEM

(71) Applicant: CLPH, LLC, Palo Alto, CA (US)

(72) Inventors: Christian S. Eversull, Palo Alto, CA (US); Stephen A. Leeflang, Sunnyvale, CA (US)

(*) Notice: Subject to any disclaimer, the term of this patent is extended or adjusted under 35 U.S.C. 154(b) by 272 days.

(21) Appl. No.: 15/960,029

(22) Filed: Apr. 23, 2018

(65) Prior Publication Data

US 2018/0304044 A1     Oct. 25, 2018

Related U.S. Application Data

(63) Continuation of application No. 14/842,828, filed on Sep. 1, 2015, now Pat. No. 9,950,142.

(60) Provisional application No. 62/044,331, filed on Sep. 1, 2014.

(51) Int. Cl.
| | |
|---|---|
| *A61M 25/01* | (2006.01) |
| *A61B 18/14* | (2006.01) |
| *A61B 18/00* | (2006.01) |
| *A61B 17/00* | (2006.01) |

(52) U.S. Cl.
CPC .... *A61M 25/0147* (2013.01); *A61M 25/0136* (2013.01); *A61B 18/1492* (2013.01); *A61B 2017/00327* (2013.01); *A61B 2018/00577* (2013.01); *A61B 2018/00821* (2013.01); *A61B 2218/002* (2013.01); *A61B 2218/007* (2013.01); *A61M 2025/0166* (2013.01)

(58) Field of Classification Search
CPC .......... A61M 25/0147; A61M 25/0136; A61M 2025/0166; A61B 18/1492
See application file for complete search history.

(56) References Cited

U.S. PATENT DOCUMENTS

| | | | | |
|---|---|---|---|---|
| 5,318,525 | A * | 6/1994 | West | A61B 18/1492 600/585 |
| 5,413,107 | A * | 5/1995 | Oakley | A61B 8/12 600/463 |
| 7,497,853 | B2 * | 3/2009 | Fischer | A61M 25/0136 604/528 |
| 2009/0281524 | A1 * | 11/2009 | Scheibe | A61M 25/0136 604/528 |

(Continued)

*Primary Examiner* — Nathan R Price
*Assistant Examiner* — Courtney B Fredrickson
(74) *Attorney, Agent, or Firm* — William A. English; Vista IP Law Group LLP

(57) ABSTRACT

Deflectable apparatus and methods for performing a procedure within a patient's body using such apparatus are provided. Generally, the apparatus includes an elongate tubular member including a proximal end, a distal end, a longitudinal axis extending between the proximal and distal ends, a deflectable distal portion including first and second lumens spaced apart from one another on generally opposite sides of the longitudinal axis, and a handle coupled to the proximal end of the tubular member. A pull wire includes a loop disposed within the handle and first and second segments extending from the loop and slidably received in the first and second lumens, respectively, and coupled to the distal end. An actuator is provided on the handle for applying tension to either the first or the second segment to cause a distal portion of the tubular member to deflect, e.g., in opposite directions.

26 Claims, 3 Drawing Sheets

(56) References Cited

U.S. PATENT DOCUMENTS

| | | | |
|---|---|---|---|
| 2012/0089125 A1* | 4/2012 | Scheibe | A61M 25/0147 604/523 |
| 2014/0276605 A1* | 9/2014 | Tejani | A61M 25/0152 604/508 |
| 2014/0323964 A1* | 10/2014 | Leeflang | A61M 25/0012 604/95.04 |
| 2015/0231366 A1* | 8/2015 | Davies | A61M 25/0136 604/95.04 |

* cited by examiner

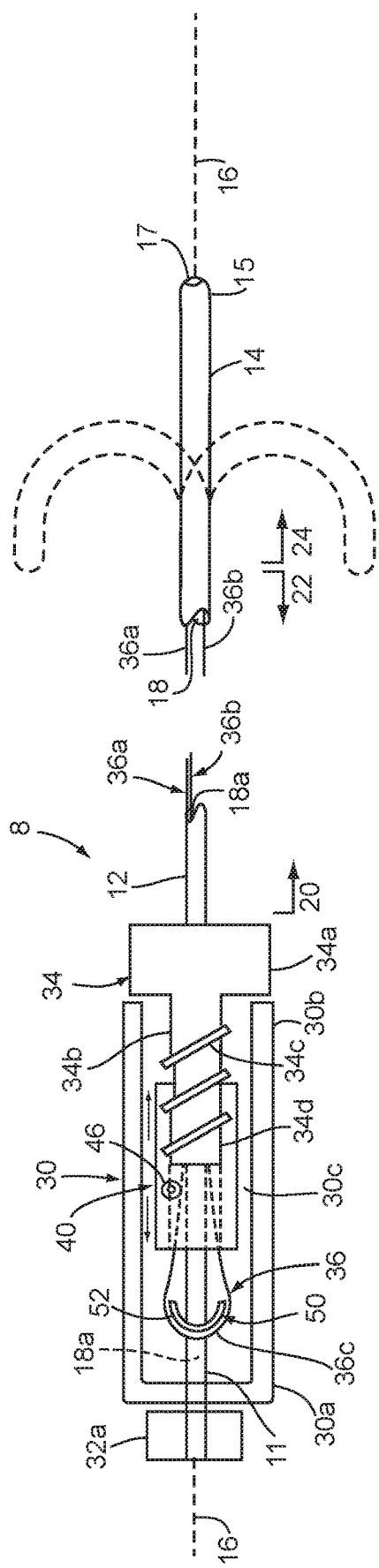
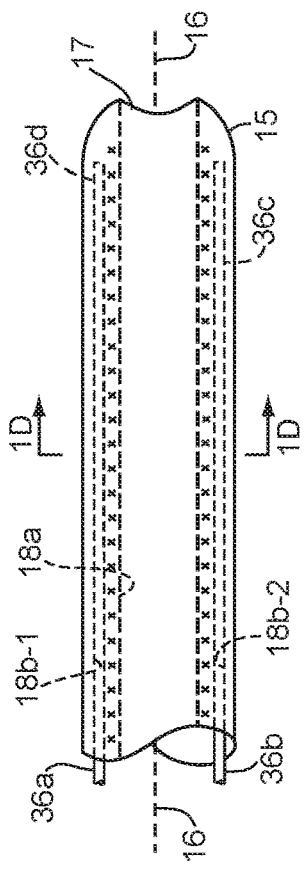
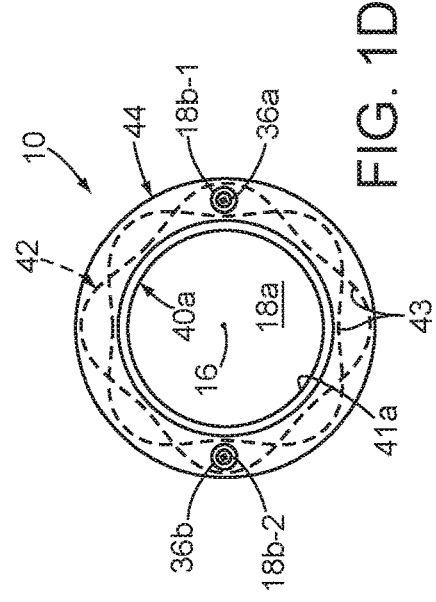
FIG. 1B
FIG. 1C
FIG. 1D

STEERABLE CATHETERS AND METHODS FOR MAKING THEM

RELATED APPLICATION DATA

This application is a continuation of co-pending application Ser. No. 14/842,828, filed Sep. 1, 2015, issuing as U.S. Pat. No. 9,950,142, claims benefit of provisional application Ser. No. 62/044,331, filed Sep. 1, 2014, the entire disclosures of which are expressly incorporated by reference herein.

FIELD OF THE INVENTION

The present invention relates generally to catheters, sheaths, or other tubular devices including steerable distal portions, and, more particularly, to handles and actuators for steerable catheters, sheaths, or other tubular devices, and to methods for making such tubular devices and/or handles.

BACKGROUND

Elongate tubular devices, such as diagnostic or treatment catheters or sheaths may be provided for introduction into a patient's body, e.g., the patient's vasculature or other body lumens. For example, a catheter may have a distal portion configured to be introduced into a body lumen and advanced to one or more desired locations within the patient's body by manipulating a proximal end of the catheter.

To facilitate introduction of such a catheter, one or more wires, cables, or other steering elements may be provided within the catheter, e.g., that are coupled to the distal portion and may be pulled or advanced from the proximal end to deflect the distal portion. For example, a steering element may be provided that is intended to deflect the distal portion within a predetermined plane and/or into a desired curved shape.

Pull wires are a common way to impart deflection ability to such a catheter. The pull wire may be slidably disposed within a lumen of the catheter that extends from the proximal end to the distal where a distal end of the pull wire is coupled to the distal end of the catheter. A proximal end of the pull wire may be coupled to an actuator provided on a handle coupled to the proximal end of the catheter. When a proximal tension is applied to the pull wire, e.g., by directing the actuator proximally, it may cause a distal portion of the catheter to curve or otherwise deflect in a first direction. However, the actuator may not be generally directed distally with equal effect to cause the distal portion to curve or deflect in a second opposite direction. Instead, a second pull wire may be provided that be offset from the first pull wire and actuated to deflect the distal portion in the second opposite direction.

Accordingly, there is a need for improved steerable catheters, sheaths, and other tubular devices and for handles and/or actuators for such tubular devices.

SUMMARY

The present invention is directed to catheters, sheaths, or other tubular devices including steerable distal portions. More particularly, the present invention is directed to handles and actuators for steerable catheters, sheaths, or other tubular devices, and to methods for making such tubular devices and/or handles.

In accordance with one embodiment, a deflectable apparatus is provided for performing a procedure within a patient's body that includes an elongate tubular member comprising a proximal end, a distal end, a longitudinal axis extending between the proximal and distal ends, a deflectable distal portion comprising first and second lumens spaced apart from one another on generally opposite sides of the longitudinal axis, and a handle coupled to the proximal end of the tubular member. A pull wire is provided that includes a loop disposed within the handle, a first segment extending distally from the loop through the tubular member and slidably received in the first auxiliary lumen and terminating at a first end coupled to the distal end of the tubular member, and a second segment extending distally from the loop opposite the first segment through the tubular member and slidably received in the second auxiliary lumen and terminating at a second end coupled to the distal end.

The apparatus includes an actuator for applying tension to either the first segment or the second segment to cause a distal portion of the tubular member to deflect, e.g., in opposite directions within a plane. For example, a carriage may be slidably disposed within the handle distal to the loop, the first segment coupled to the carriage at a predetermined distance from the loop. An actuator may be rotatably mounted to the handle and coupled to the carriage for directing the carriage between neutral, proximal, and distal positions within the handle.

In an exemplary embodiment, rotation of the actuator in a first direction with the carriage in the neutral position causes the carriage to move towards the proximal position to apply tension on the first segment and deflect the distal portion in a first direction, and rotation of the actuator in a second direction opposite the first direction with the carriage in the neutral position causes the carriage to move towards the distal position to apply tension on the second segment and deflect the distal portion in a second direction generally opposite the first direction.

In one example, a redirection element may be mounted in the handle proximal to the carriage, and the loop may move relative to the redirection element to apply desired tension to the pull wire. In one embodiment, the redirection element may be a curved wall defining a convex surface directed towards a proximal end of the handle, and wherein the loop may be slidably received around the convex surface such that movement of the carriage between the neutral, proximal, and distal positions causes the loop to slide around the convex surface. In another embodiment, the redirection element may be a U-shaped tube mounted in the handle and the loop may be slidably received in a lumen of the tube.

Optionally, the apparatus may also include a tensioning element for applying a desired tension on the pull wire, e.g., to minimize slack. In one embodiment, the tensioning element may include a pulley movably mounted within the handle at a location such that a portion of the pull wire travels at least partially around the pulley to adjust tension on the pull wire. In another embodiment, where the redirection element is a U-shaped tube, a central portion of the tube is substantially fixed relative to the handle, and wherein ends of the tube are movable to adjust tension on the pull wire. For example, the ends of the tube may be biased away from one another and the loop may be received through the lumen of the tube to cause the ends of the tube to move towards one another to apply a predetermined tension on the pull wire.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1B is a longitudinal cross-sectional view of the catheter of FIG. 1A, showing an exemplary embodiment of an actuator within the handle.

FIG. 1C is a longitudinal cross-sectional view of the distal portion of the catheter of FIG. 1A, showing auxiliary lumens receiving respective pull wires.

FIG. 1D is a cross-sectional view of the distal portion of the catheter of FIGS. 1A-1C taken along plane 1D-1D.

DETAILED DESCRIPTION OF THE EXEMPLARY EMBODIMENTS

Figure 1A:
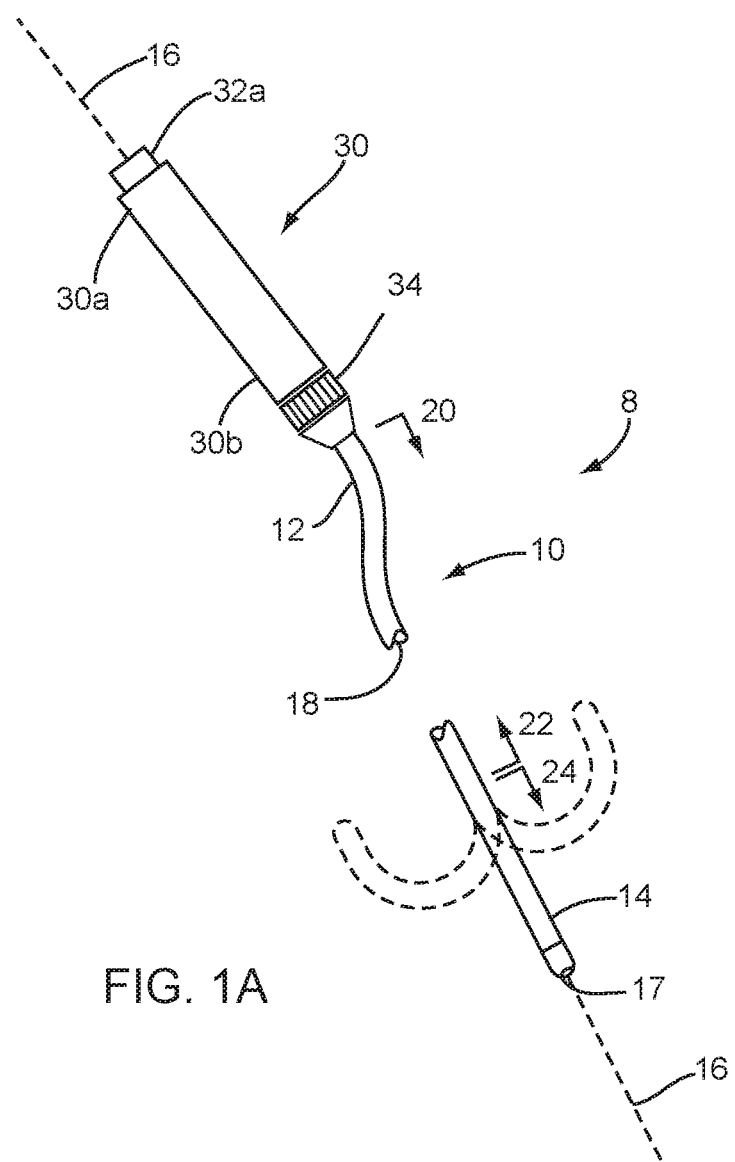
FIG. 1A is a perspective view of an exemplary embodiment of a catheter, including a steerable distal portion and a handle having an actuator for controlling deflection of the distal portion.

Turning to the drawings, FIGS. 1A-1C show an exemplary embodiment of an apparatus 8 for introduction into a body lumen (not shown), e.g., for performing a diagnostic and/or therapeutic procedure within a patient's body. In exemplary embodiments, the apparatus 8 may be a guide catheter, a sheath, a procedure catheter, e.g., an imaging catheter, an ablation and/or mapping catheter, a balloon catheter, or other tubular device sized for introduction into a body lumen, such as a vessel within a patient's vasculature, a passage within a patient's gastrointestinal tract, urogenital tract, reproductive tract, respiratory tract, lymphatic system, and the like (not shown). In exemplary embodiments, the apparatus 8 may have a length between about ten and one hundred ten centimeters (10-110 cm), and an outer diameter between about four and twenty-four French (4-24 Fr).

Generally, the apparatus 8 includes an elongate tubular member 10 including a proximal end 12, a distal end 14 sized for insertion into a body lumen, a central longitudinal axis 16 extending between the proximal and distal ends 12, 14, and one or more lumens 18 extending between the proximal and distal ends 12, 14. For example, as shown in FIGS. 1B and 1C, the apparatus 8 may include a central or primary lumen 18a, e.g., sized for receiving or carrying one or more instruments or other elements (not shown) therethrough. In exemplary embodiments, the central lumen 18a may be sized for receiving or carrying a guide wire, procedure catheter, balloon catheter, ablation catheter, cardiac lead, needle, or other instrument (not shown), one or more wires or other conductors, one or more optical fibers, one or more tubes or accessory lumens, one or more mechanical elements, one or more sensors, and/or sized for delivering and/or removing fluids or other flowable agents or materials therethrough.

In one embodiment, the central lumen 18a may exit at or communicate with an outlet 17 in the distal end 14, e.g., to allow a guidewire or other instrument (not shown) to pass therethrough and/or for delivering or aspirating fluid therethrough. In an alternative embodiment, the central lumen may be enclosed, e.g., terminating within or adjacent the distal end 14, e.g., by an electrode, cap, or other component (not shown) to isolate the central lumen 18a and/or elements carried therein from the environment outside the apparatus 8. In an exemplary embodiment where the apparatus 8 is an ablation and/or mapping catheter, the central lumen 18a may carry one or more wires or other conductors, thermocouple wires, tubes, and the like (not shown), e.g., coupled to electrodes or other elements (also not shown) carried on the distal end 14.

Returning to FIG. 1C, in addition to the central lumen 18a, the tubular member 10 includes a pair of auxiliary lumens 18b, e.g., extending adjacent the central lumen 18a along at least a distal portion 24 of the tubular member 10, e.g., substantially parallel to and offset from one another on opposite sides of the central axis 16. In an exemplary embodiment, each auxiliary lumen 18b may be configured to receive a segment of a pull wire or other steering element 36 therein, e.g., to bend or otherwise deflect the distal portion 24 of the tubular member 10, as described further below. Optionally, the tubular member 10 may include one or more additional lumens (not shown), e.g., one or more additional steering element lumens, inflation lumens (e.g., if the apparatus 8 includes one or more balloons, not shown on the distal end 14), and/or accessory lumens.

In addition, the apparatus 8 includes a handle 30 coupled to the proximal end 12 of the tubular member 10 that includes one or more actuators, e.g., a rotatable actuator 34 for deflecting a distal portion 24 of the tubular member in a desired manner, as described further elsewhere herein. For example, the actuator 34 may be coupled to the steering element 36 for selectively pulling first and second segments 36a, 36b received in the auxiliary lumens 18b such that proximal tension applied to one of the segments 36a, 36b causes the distal portion 24 to curve or otherwise deflect in a desired manner, e.g., in a simple curve within a plane or otherwise as described elsewhere herein.

The auxiliary lumens 18b may extend separately from the distal end 14 proximally through intermediate and proximal portions 22, 20 to the handle 30 such that a single steering element 36 may be used that includes a loop 36c disposed within the handle 30, as described further elsewhere herein. As shown in FIG. 1C, the auxiliary lumens 18b may be positioned, over at least a portion of the catheter length, substantially away from the central lumen 18a along the distal portion 24, e.g., to maximize a bending moment applied to the distal portion 24 when proximal tension is applied to one of the segments 36a, 36b. Along the intermediate and/or proximal portions 22, 20, the auxiliary lumens 18b may transition to locations closer to the central axis 16, e.g., to minimize any bending moment applied proximal to the distal portion 24. Alternatively, a single lumen (not shown) may be provided along the intermediate and/or proximal portions 22, 20 that separates and/or otherwise communicates with the lumens 18b-1, 18b-2 in the distal portion 24.

For example, within the handle 30, a proximal extension 11 may be provided that extends from the proximal end 12 of the tubular member 10 through the handle 30. The proximal extension 11 may be coupled to and/or communicate with the hub or port 32a on the handle 30, e.g., including a lumen that communicates with the primary lumen 18a of the tubular member 10. Optionally, the proximal extension 11 may include one or more additional lumens (not shown), e.g., for receiving one or both of the segments 36a, 36b of the pull wire, as described further below. The hub/port 32a may be adjustably coupled to the handle 30 such that the rotational position of the tubular member 10 may be adjusted, e.g., by adjusting and/or fixing the position of the hub/port 32a relative to the handle 30. The proximal extension 11 may be coupled to a proximal end 30a of the handle 30 to secure the tubular member 10 relative to the handle 30 yet may remain uncoupled to a distal end 30b of the handle 30, also as described further below.

Returning to FIG. 1A, the distal end 14 of the tubular member 10 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, ablation elements, thermocouples, steering mechanisms, imaging devices, helical anchors, needles, and the like (not shown), depending upon the particular intended application for the apparatus 8. Further, in addition or alternatively, the distal end 14 may include one or more features to enhance radiopacity and/or visibility under ultrasound, MRI or other imaging modalities, e.g., by mounting one or more platinum elements on the distal end 14, doping one or more regions of the distal end 14 with tungsten or barium sulfate, and/or other methods known in the art.

Generally, with particular reference to FIG. 1D, the tubular member 10 may be constructed to include an inner liner 40, e.g., at least partially or entirely surrounding or otherwise defining the central lumen 18a, a reinforcement layer 42 surrounding the inner liner 40, and an outer jacket 44 surrounding the reinforcement layer 42, each of which may extend at least partially between the proximal and distal ends 12, 14 of the tubular member 10. The reinforcement layer 42 and/or outer jacket 44 may be attached to the inner liner 40, e.g., by laminating, adhering, adhesive bonding, ultrasonic welding, reflowing or other heating, and the like, as described elsewhere herein.

In an exemplary embodiment, the central lumen 18a is defined by an inner liner 40a including an inner surface 41a. The inner liner 40a may be formed from lubricious material, e.g., PTFE, to provide a lubricious inner surface 41a. Alternatively, the inner liner 40 may be formed from one or more layers of thermoplastic or other polymeric material including one or more coatings on the inner surface 41a having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Optionally, an inner liner may also at least partially surround each of the auxiliary lumens 18b (not shown), which may be formed from a lubricious material and/or may include one or more coatings on its inner surface, similar to the inner liner 40a. The inner surface of the auxiliary lumens 18b may have a substantially uniform cross-section. Alternatively, the inner surface of the auxiliary lumen 18b may have a textured or other variable cross-section along, e.g., along its length and/or about its circumference.

Optionally, any or all of the inner liner 40a, reinforcement layer 42, and/or outer jacket 44 may be formed from multiple layers of like or different materials (not shown), e.g., to provide desired material properties in the different portions of the tubular member 10. In an exemplary embodiment, the outer jacket 44 may be formed from PEBAX, nylon, urethane, and/or other thermoplastic material, e.g., such that the material of the outer jacket 44 may be heated and reflowed and/or otherwise formed around the components defining the lumens 18, e.g., as described elsewhere herein.

In one embodiment, one or more of the layers of the tubular member 10 may have a substantially homogenous construction between the proximal and distal ends 12, 14. Alternatively, the construction may vary along the length of the tubular member 10 to provide desired properties, e.g., between proximal, intermediate, and distal portions 20, 22, 24. For example, a proximal portion 20 of the tubular member 10 adjacent the proximal end 12 may be substantially rigid or semi-rigid, e.g., providing sufficient column strength to allow the distal end 14 of the tubular member 10 to be pushed or otherwise manipulated from the proximal end 12, while the distal portion 24 may be substantially flexible. As described further below, the distal portion 24 of the tubular member 10 may be steerable, i.e., may be bent, curved, or otherwise deflected substantially within a steering plane.

The reinforcement layer 42 may include one or more reinforcing members 43, e.g., wound in a braided or other helical configuration around the inner liner 40a, and the outer jacket 44 may include one or more tubular layers surrounding the reinforcement layer 42 and/or between the reinforcement layer 42 and the inner liner 40a. In an exemplary embodiment, the reinforcement layer 42 may include one or more, or a plurality of, round or flat (e.g., rectangular, elliptical, or flat oval) wires, filaments, strands, or other reinforcement members, e.g., formed from metal, such as stainless steel, plastic, glass, woven or twisted fibers, such as aramid, and the like, or composite materials.

The reinforcement layer 42 may be configured to substantially transfer torsional forces between the proximal and distal ends 12, 14, e.g., to allow the tubular member 10 to be twisted from the proximal end 12 to rotate the distal end 14 about the longitudinal axis 16 within a patient's body. In addition, the reinforcement layer 42 may allow the distal end 14 of the tubular member 10 to be advanced or otherwise manipulated within a patient's body from the proximal end 12 without substantial risk of buckling and/or kinking. Optionally, the pitch of the reinforcement layer 42 may be varied along the length of the tubular member 10, as desired, e.g., in order to optimize mechanical properties of various segments or portions of the tubular member 10.

In the exemplary embodiment shown in FIG. 1D, the reinforcement members 43 may be applied around the central lumen 18a such that some of the reinforcement members 43a including windings that pass between the central lumen 18a and the auxiliary lumens 18b when wrapped around the central lumen 18a, and some of reinforcement members including windings 43b that surround both the central lumen 18a and the auxiliary lumen 18b. Exemplary configurations and methods for making such tubular members are described in U.S. Publication No. 2014/0323964, the entire disclosure of which is expressly incorporated by reference herein.

In an exemplary embodiment, the auxiliary lumens 18b may be radially offset from the central axis 16 substantially along the length of the tubular member 10, e.g., entirely from the distal end 14 to the proximal end 12, thereby offset from a center of mass of the tubular member 10 along its length. In this embodiment, the non-steerable portions of the tubular member 10 may be constructed to resist bending, e.g., having a substantially greater stiffness than the distal portion 24, such that any bending moment generated by a pull wire is applied primarily to the distal portion 24.

Alternatively, along at least the proximal portion 20 and, optionally, along the intermediate portion 22, a single auxiliary lumen may be provided that receives both segments 36a, 36b of the pull wire 36 (not shown). In this alternative, the intermediate and/or proximal regions 20, 20 may be constructed to offset the center of mass from the central axis 16, e.g., to align the center of mass with the single auxiliary lumen within the intermediate and/or proximal portions 22, 20 (not shown). For example, the tubular member 10 may have a non-circular or other asymmetrical cross-section that minimizes applying a bending moment to the intermediate and/or proximal portions 22, 20, thereby applying any bending moment substantially only to the distal portion 24.

Optionally, the handle 30 may also include one or more ports, e.g., port 32a communicating with the central lumen 18a, or other respective lumens (not shown). Optionally, the port 32a may include one or more valves, e.g., a hemostatic valve (also not shown), which may provide a substantially fluid-tight seal, while accommodating insertion of one or more instruments or fluids into the central lumen 18a. In addition or alternatively, a side port (not shown) may be provided on the handle 30, e.g., for delivering fluid into and/or aspirating fluid from the primary lumen 18a, e.g., around an instrument inserted into the primary lumen 18a. Optionally, the handle 20 and/or proximal end 12 may include one or more connectors, such as luer lock connectors, electrical connectors, and the like, for connecting other devices (not shown) to the apparatus 10, such as syringes, displays, controllers, and the like (also not shown). In addition, the handle 30 may include one or more actuators, such as sliders, buttons, switches, rotational actuators, and the like, e.g., for activating and/or manipulating components (also not shown) on the distal end 14 or otherwise operating the apparatus 10.

With particular reference to FIGS. 1A and 1B, a rotating knob 34 or other actuator, e.g. a sliding actuator, lever actuator, and the like, may be provided on the handle 30 that is coupled to the pull wire 36 by a carriage 40 to deflect the distal portion 24 in a desired manner, e.g., from a neutral position (e.g., a substantially straight configuration shown in FIG. 1B) to a first deflected configuration (e.g., curved upwardly as shown in phantom in FIG. 1B) and/or a second deflect configuration (e.g., curved downwardly as shown in phantom in FIG. 1B), as described further below. In this manner, a single pull wire or steering element 36 may provide bi-directional deflection of the distal portion 24.

In particular, as shown in FIG. 1B, the pull wire 36 may include a loop 36c disposed within the handle 30, e.g., cooperating with a redirection element 50 mounted within handle 30, e.g., adjacent the proximal end 30a of the handle 30. The elongate segments 36a, 36b may extend enter a lumen of the proximal extension 11 (or separate lumens), e.g., via one or more slots or other openings in a side wall of the proximal extension 11 (not shown) and extend distally from the handle 30, i.e., through the proximal and intermediate portions 20, 22 of the tubular member 10 into the respective auxiliary lumens 18b-1, 18b-2 shown in FIG. 1C.

The segments 36a, 36b may be slidably received in the auxiliary lumens 18b within the distal portion 24 while distal ends 36d, 36e of the pull wire 36 may be coupled to the distal end 14 of the tubular member 10, e.g., adjacent the distal tip 15, e.g., to a cap, ring, and/or other structure (not shown) on the distal end 14. With the segments 36a, 36b otherwise free to slide relative to the auxiliary lumens 18b, an axial force on either segment 36a, 36b, e.g., a proximal force due to pulling on the segment 36s, 36b from the handle 30 may apply a bending moment to the distal portion 24, thereby causing the distal portion 24 to curve or otherwise deflect. For example, with additional reference to FIG. 1B, a proximal force applied to the first segment 36a within the handle 30 may cause the distal portion 24 to bend upwardly, while a proximal force applied to the second segment 36b may cause the distal portion 24 to bend downwardly, e.g., within the same plane, as indicated by the curved distal portion 24 shown in phantom in FIG. 1B.

The steering element 36 may be formed from materials capable of substantially transferring any axial forces applied at the proximal end 12 to the distal end 14, as is known in the art. Optionally, the steering element 36 may include a coating, e.g., PTFE, parylene, silicone, or other lubricious material, an outer sleeve, e.g., formed from HDPE, PTFE, and the like, to reduce friction between the segments 36a, 36b and the wall of the respective auxiliary lumen 18b. Alternatively or in addition, the inner surface of the auxiliary lumens 18b may be formed from lubricious material and/or may include one or more coatings, as described elsewhere herein. Alternatively or in addition, the auxiliary lumen 18b may include one or more incompressible elements, e.g., a tightly wound coil therearound, e.g., to prevent compression, which may otherwise lead to creating a bending moment along at least part of its length.

With further reference to FIG. 1B, the handle 30 may include one or more components coupled to the actuator 34 for selectively applying a pulling force on one of the segments 36a, 36b. For example, the actuator 34 may include a rotatable knob 34a mounted to the handle 30, e.g., adjacent the distal end 30b thereof, and a screw 34b coupled to the knob 34a that extends into an interior 30c of the handle 30, e.g., substantially parallel to the central axis 16 from the distal end 30b partially towards the proximal end 30a of the handle 30.

A carriage 40 is slidably disposed within the interior 30c of the handle 30, e.g., between the proximal and distal ends 30a, 30b that may be movable axially without rotation, e.g., by providing a track or other guide (not shown) within the handle 30 that allows axial movement anywhere between a proximal position and a distal position. The handle interior 30c may include one or more adjustable and/or removable stops, e.g., pins, spacers, tabs, and the like (not shown), designed to limit the travel of the carriage 40 within the handle 30 to a predetermined range, e.g., to limit or set the amount of deflection that may be achieved by the distal portion 24. Alternatively, the range of travel may be selectively adjusted during assembly, e.g. to provide consistent performance across devices despite small variations in positioning, length, compressibility, and or other mechanical characteristics. The carriage 40 may be coupled to the screw 34b, e.g., by one or more helical threads or other elements such that rotation of the knob 34a causes the screw 34b to rotate relative to the handle 30 (without axial movement), thereby translating the carriage 40 axially within the handle 30. For example, as shown, the screw 34b may include one or more threads 34c extending helically around a tubular shaft 34d and the carriage 40 may include one or more cooperating threads, teeth, and the like that slidably engage one another to transfer rotation of the screw 34b into axial movement of the carriage 40. The configuration of the thread(s), e.g., thread angle, thickness, and/or spacing, may be set such that a desired amount of rotation translates into full proximal or distal movement of the carriage 40, e.g., from a neutral position.

The carriage 40 and screw 34b may include axial passages therethrough along the central axis 16 to accommodate the proximal extension 11 passing through them, e.g., such that proximal extension 11 may extend from the proximal end 30a of the handle 30 to the proximal end 12 of the tubular member 10 outside the handle 30 (or the proximal end of the tubular member 10 may enter the handle 30). Thus, the carriage 40 may move axially over the proximal extension 11.

In addition, the handle 30 also includes a redirection element 50 that may be mounted within the interior 30c proximal to the carriage 40, e.g., adjacent the proximal end 30a of the handle 30, that may cooperate with the loop 36c of the pull wire 34 to accommodate movement of the segments 36a, 36b of the pull wire 34. In the embodiment shown in FIG. 1B, the redirection element is a curved wall 50 defining a convex surface 52 oriented towards the proximal end 30a of the handle 30 such that the loop 36c is slidably received around the convex surface 52 and the segments 36a, 36b extend distally, e.g., into the tubular extension 11 and into the tubular member 10, as described elsewhere herein. Optionally, the curved wall 50 may be formed from lubricious material, e.g., HDPE, LDPE, nylon, PTFE, FEP, and the like, and/or the convex surface 52 may be coated with a lubricious coating, e.g., a hydrophilic coating or the like, to reduce friction and/or otherwise facilitate the pull wire 36 sliding around the convex surface 52.

The first segment 36a of the pull wire 36 may be coupled to the carriage 40, e.g., at a predetermined distance from the loop 36c and/or redirection element 50. For example, the carriage 40 may include a set screw or other fastener 46 that may engage a region of the first segment 36a, thereby coupling movement of the region to movement of the carriage 40. In addition or alternatively, the first segment 36a may be bonded, welded, soldered, and/or otherwise attached to the carriage 40. One advantage of a fastener is that the region of the first segment 36a engaged by the fastener 46 may be adjusted if desired, e.g., during final assembly and/or configuration of the apparatus 10, by loosening the fastener 46, moving the first segment 36a axially, and then securing the fastener 46 again. For example, after ensuring that the distal portion 24 is in a neutral, e.g., substantially straightened, configuration with forces balances between the first and second segments 36a, 36b, the fastener 46 may then be used to secure the first segment 36a to the carriage 40. Alternatively, the carriage 40 may include an attachment mechanism (not shown) that is constructed to attach to the first and/or second segments 36a, 36b. The attachment mechanism may be adjustably coupled to the carriage 40 such that its position relative to the carriage 40 may be easily adjusted, thereby altering the position of the attachment point of the segments 36a, 36b to the carriage 40.

With the first segment 36a coupled to the carriage 40, movement of the carriage 40 causes the pull wire 36 to move and slide around the convex surface 52. In particular, if the carriage 40 is directed proximally (e.g., by rotating the actuator 34 in a first direction), a proximal pulling force is applied to the first segment 36a of the pull wire 36 (distally beyond the secured region), thereby causing the distal portion 24 to deflect, e.g., upwardly as shown in FIG. 1B and described elsewhere herein. The portion of the pull wire 36 defining the loop 36c may slide around the convex surface 52, thereby lengthening the second segment 36b of the pull wire 36 and shortening the first segment 36a (relative to the loop 36c), which may prevent slack from occurring along the pull wire 36.

Conversely, if the carriage 40 is directed distally (e.g., by rotating the actuator in a second direction opposite the first direction), a distal pulling force may be applied to the first segment 36a of the pull wire 36 (proximal to the secured region), which may translate through the loop 36c to apply a proximal force to the second segment 36b, thereby causing the distal portion 24 to deflect in the opposite direction, e.g., downwardly as shown in FIG. 1B. Again the portion of the pull wire 36 defining the loop 36c may slide around the convex surface 52, thereby lengthening the first segment 36a of the pull wire 36 and shortening the second segment 36b (relative to the loop 36c). The second segment 36b may slidably pass through the carriage 40, e.g., in order to guide its path through the handle 30.

During manufacturing and/or assembly of the apparatus 8, the tubular member 10 may be fabricated using known materials and/or methods, such as those described in U.S. Publication No. 2014/0323964, incorporated by reference herein. The components of the handle 30, e.g., including the actuator 34, carriage 40, and/or redirection element 50 may also be formed using known materials, e.g., plastic, metal, or composite materials, and methods, e.g., molding, casting, machining, and the like. For example, the outer casing of the handle 30 may be formed from a pair of clamshell halves (not shown) molded or otherwise formed to allow access to the interior 30c for positioning the internal components, as desired. Some features, such as the curved wall 50 and/or track or guide (not shown) for the carriage 40 may be integrally molded or otherwise formed into one or both of the halves. After the internal components are assembled, the halves may be substantially permanently attached together, e.g., using one or more of cooperating connectors, bonding with adhesive, fusing, and the like.

For example, the proximal extension 11 may be positioned within the interior and coupled to the proximal end 30a of the handle 30, e.g., again using one or more of cooperating connectors, bonding with adhesive, fusing, and the like, and then the carriage 40 and screw 34b may be inserted over the proximal extension 11 such that the carriage 40 is slidable along the track or guide and the knob 34a of the actuator 34 is positioned adjacent the distal end 30b of the handle 30.

The pull wire 36 may be placed within the handle 30, e.g., by directing a central region around the convex surface 52 of the curved wall 50. Optionally, the carriage 40 may include one or more passages or apertures (not shown) for slidably receiving a portion of the segments 36a, 36b, e.g., to guide the pull wire 36 from the loop 36c into the proximal extension 11 and/or otherwise out the distal end 30b of the handle 30.

The segments 36a, 36b of the pull wire 36 may be directed into the proximal end 12 of the tubular member 10, e.g., into a single or separate auxiliary lumens along the proximal portion 20 and/or intermediate portion 22, and then into the separate auxiliary lumens 18b-1, 18b-2 shown in FIG. 1C. The proximal end 12 of the tubular member 10 may be attached to the proximal extension 11, e.g., adjacent the distal end 30b of the handle 30 also using known methods, e.g., one or more of cooperating connectors, bonding with adhesive, fusing, and the like. Alternatively, the proximal extension 11 may be a continuation of the tubular member 10. The auxiliary lumens 18b-1 and 18b-2 may extend into the proximal extension 11 and exit the sidewall thereof, e.g., midway through the handle 30. The ends 36d, 36e of the pull wire 36 may be coupled to the distal end 14 of the tubular member 10, e.g., before or after attaching the tubular member 10 to the proximal extension 11, and/or before or after a shaft assembly, e.g., including the tubular member 10 and proximal extension 11, is placed into the handle 30. For example, the ends 36d, 36e may be attached to the distal end 14 itself, e.g., again using one or more of cooperating connectors, bonding with adhesive, fusing, and the like. Alternatively, the ends 36d, 36e may be coupled to a cap, ring, or other component (not shown) attached to the distal end 14, as described elsewhere herein.

Before coupling the ends 36d, 36e of the pull wire(s) 36, desired excess pull wire material may be cut or otherwise removed, e.g., to provide a desired length extending through the tubular member 10 to the loop 36c within the handle 30. The first segment 36a of the pull wire may be coupled to the carriage 40, e.g., using one or more fasteners or other methods, as described elsewhere herein, before or after coupling the ends 36d, 36e to the distal end 14. The ends 36a and 36b of the pull wire(s) 36 may be joined to form a loop 36c and/or the segments 36a, 36b may be attached at a common location, e.g., to the carriage 40 as described elsewhere herein.

For example, the relative length and tension applied to the segments 36a, 36b may be set to minimize slack within the apparatus 8 and/or to balance the inherent tensions in the segments 36a, 36b, e.g., to bias the distal portion 24 of the tubular member 10 to a desired neutral configuration, e.g., a substantially straightened or other desired shape. Optionally, a desired compressive force may be applied to the tubular member 10, e.g., between the proximal and distal ends 12, 14 before finally coupling the pull wire 36 such that segments 36a, 36b remain under a predetermined axial tension. The tubular member 10 and/or proximal extension 11 may be constructed to provide a predetermined axial tension. For example, a portion of the tubular member 10 and/or proximal extension 11 may be constructed of an elastically compressible material, e.g., urethane, PEBA, and the like, of a predetermined durometer, thickness, and/or length in order to achieve a desired spring effect.

Alternatively or in addition, the tubular member 10 and/or proximal extension 11, e.g., the catheter shaft may include a range of stiffnesses and/or transitions along its length, e.g., as described elsewhere herein, for the purpose of disposing bending to a distal segment. Additionally, the segment of the shaft passing through the handle 30 may be selectively reinforced, e.g., to resist axial compression in order to further concentrate compression and thereby bending action at the distal portion 24 of the tubular member 10, e.g., to provide more responsive deflection of the distal portion 24. Reinforcement of the proximal portion 20 may be achieved by thickening the wall substantially, e.g., compared to the intermediate and/or distal portion 22, 24 of the tubular member 10, e.g., sized to enter the body, by altering the reinforcing layer, e.g., optimizing the braid pattern for compression resistance, by including axial reinforcing member in the proximal wall of the shaft, e.g., wires, cables, and the like, and/or by overlaying a compression resistant element, e.g., a hypotube and the like over the proximal shaft.

In another alternative, a pair of pull wires (not shown) may be provided that include distal ends coupled to the distal end 14 of the tubular member 10 (e.g., by welding the distal ends of the pull wires to a ring or other component on the distal end 14) and extend proximally through the auxiliary lumens 18b into the handle 30. The pull wires may then exit through the side wall of the proximal portion (or extension) of the tubular member 10, e.g., through side wall openings within the handle 30, and one or both pull wires may be partially wrapped around the redirection element 50 and proximal ends of the pull wires may be attached or otherwise coupled together, thereby defining the loop 36c that extends around the redirection element 50. Before the pull wires are coupled together, the pull wires may be pulled to stretch or compress the tubular member 10 as desired, e.g., to apply a desired tension to the pull wires, and any excess pull wire may be cut or otherwise removed.

Figure 2:
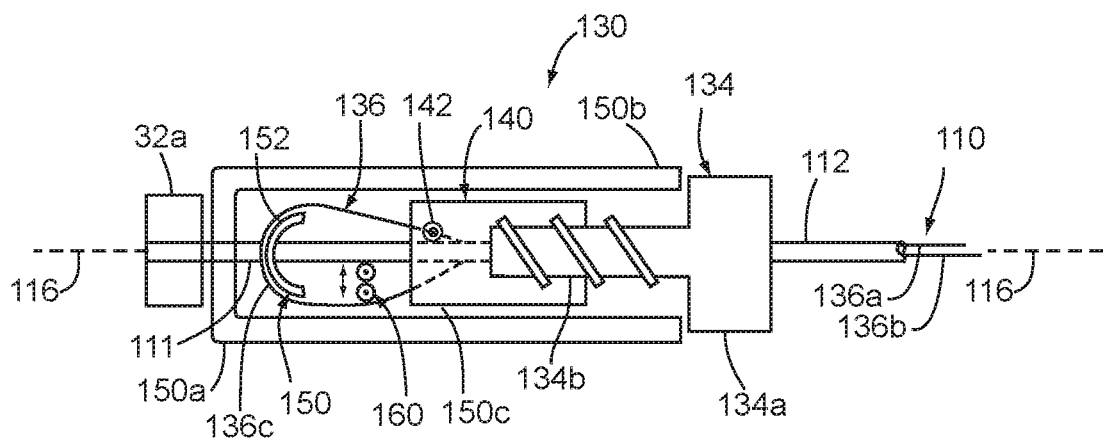
FIG. 2 is a cross-sectional detail of an example of a handle including an exemplary embodiment of a tensioning element for applying a desired tension to a pull wire of the catheter.

In addition or alternatively, a tensioning element may be provided within the handle 30 to apply a desired tension to the segments 36a, 36b. For example, as shown in FIG. 2, another embodiment of a handle 130 is shown (with like features identified with similar reference numbers but increased by 100) that includes a proximal extension 111, an actuator 134, a carriage 140, and 1 redirection element 150, generally similar to other embodiments herein. The handle 130 or hub 132a is coupled to a proximal end 112 of a tubular member 110 or proximal end of the extension 111, and a single pull wire 136 is provided that includes a loop 136c that extends around a convex surface 152 of the redirection member 150 and segments 136a, 136b that extend into the tubular member 110, e.g., to the distal end (not shown), also similar to other embodiments herein.

In addition, the handle 130 includes a tensioning element 160 mounted therein that cooperates with one of the segments 136b to adjust and/or apply a desired tension to one or both of the segments 136a, 136b. As shown in FIG. 2, the tensioning element 160 includes a pulley 160 that is rotatably mounted within the interior 150c of the handle 150 such that a portion of the segment 136b of the pull wire 136 travels at least partially around the pulley 160 to adjust tension on the pull wire, e.g., before entering the carriage 140 and/or proximal extension 111.

Optionally, the location of the pulley 160 may be adjusted, e.g., closer to or further away from the central axis 116, as shown in FIG. 2, thereby increasing or decreasing tension on the segments 136a, 136b. For example, a fastener may secure the pulley 160 in a track or slot (not shown), which may be loosened to adjust the location of the pulley 160 and then secured at a desired position along the track or slot to apply a desired tension on the pull wire 136. In an alternative embodiment, the pulley may be replaced by a guide or other surface that is generally lubricious allowing the one or more segments 136 to slide across it freely.

In an alternative embodiment, the pulley 160 may be movably mounted within the handle 136 and biased to a first position, e.g., away from the central axis 116 by a spring (not shown), yet movable towards a second position, e.g., closer to the central axis 116, such that the ends of the pull wire 136 (not shown) may subjected to a desired tension before securing them to the distal end of the tubular member 110, thereby causing the pulley 160 to move away from the first position and the resulting bias applying a predetermined tension on the pull wire.

Figure 3:
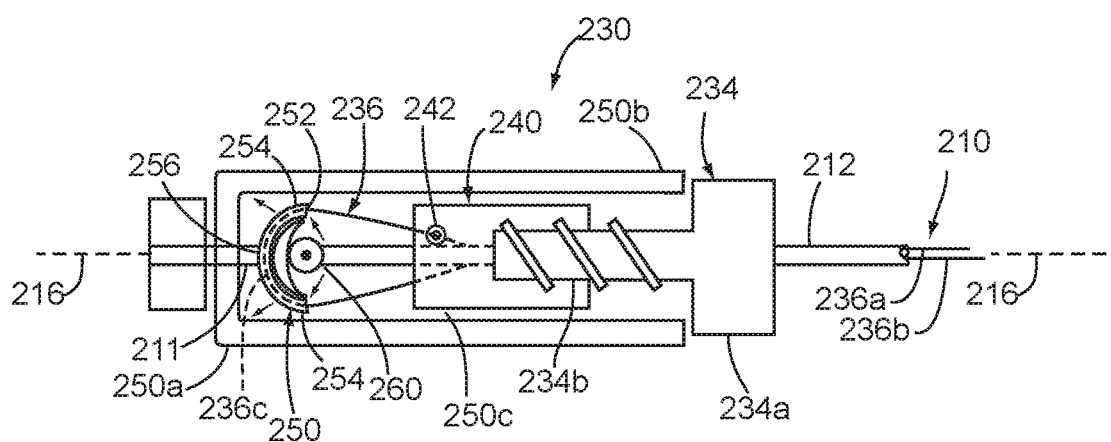
FIG. 3 is a cross-section detail of another example of a handle including another exemplary embodiment of a redirection element and a tensioning element for applying a desired tension to a pull wire of the catheter.

Turning to FIG. 3, yet another embodiment of a handle 210 is shown (with like features identified with similar reference numbers but increased by 200) that includes a proximal extension 211, an actuator 234, and a carriage 240, generally similar to other embodiments herein. The handle 230 may be coupled to a proximal end 212 of a tubular member 210 or the tubular member 212 may enter the handle unattached, and a single pull wire 236 is provided that includes a loop 236c and segments 236a, 236b that extend into the tubular member 210, e.g., to the distal end (not shown).

Unlike the previous embodiments, the redirection element 250 is a U-shaped tube defining a lumen 252 in which the loop 236c of the pull wire 236 may be slidably received. Thus, as the pull wire 236 is actuated, the pull wire 236 may slide through the lumen 252 such that the tube 250 redirects the tension on the second segment 236b, similar to other embodiments herein.

Optionally, the handle 230 may include a tensioning element 260 mounted within an interior 250c of the handle 250 that cooperates with the tube 250 to adjust and/or apply a desired tension to one or both of the segments 236a, 236b. As shown, the tensioning element 260 may include a spring 260 mounted adjacent the tube 250 for biasing ends 254 of the tube 250 away from one another. For example, a central portion 256 of the tube 250 may be substantially fixed relative to the handle 230, yet the ends 254 may be movable, e.g., to define a higher or lower radius arc. In particular, the ends 254 may be biased to an inner or relatively lower radius arc and the spring 260 may include arms that are biased to push against the ends 254, e.g., to direct the ends 254 outwardly to a relatively higher radius arc. When the loop 236c of the pull wire 236 is received through the lumen 252 of the tube 250, the ends of the pull wire 236 may be coupled such that a desired tension is applied to the segments 236a, 236b by the spring 260 and ends 252 of the tube 250. The tube 250 may be flexible and lubricious, e.g., constructed of HDPE, LDPE, PTFE, FEP, and the like.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A deflectable apparatus for performing a procedure within a patient's body, comprising:
   an elongate tubular member comprising a proximal end, a distal end sized for introduction into a patient's body, a central longitudinal axis extending between the proximal and distal ends, and a deflectable distal portion, and further comprising first and second auxiliary lumens spaced apart from one another on generally opposite sides of the longitudinal axis;
   a handle coupled to the proximal end of the tubular member, the tubular member comprising a proximal extension extending proximally from the proximal end through the handle and coupled to a proximal end of the handle such that the tubular member remains uncoupled to a distal end of the handle;
   a pair of pull wires including distal ends welded to a distal ring adjacent the tubular member distal end and extending proximally through the auxiliary lumens until exiting through side wall openings in the proximal extension of the tubular member within the handle, the pair of pull wires terminating proximally in first and second ends, respectively, that are joined to form a single loop by attachment at a common location to a carriage within the handle, the loop extending around a redirection element mounted within the handle;
   the carriage slidably disposed within the handle distal to the redirection element; and
   an actuator rotatably mounted to the handle over the proximal extension adjacent the distal end of the handle and coupled to the carriage for directing the carriage between neutral, proximal, and distal positions within the handle, such that rotation of the actuator in a first direction with the carriage in the neutral position causes the carriage to move towards the proximal position to apply tension on the first end and deflect the distal portion in a first direction, and rotation of the actuator in a second direction opposite the first direction with the carriage in the neutral position causes the carriage to move towards the distal position to apply tension on the second end and deflect the distal portion in a second direction generally opposite the first direction.

2. The apparatus of claim 1, wherein the handle comprises one or more adjustable stops configured to limit travel of the carriage within the handle to a predetermined range.

3. The apparatus of claim 1, wherein the carriage comprises one or more passages or apertures for slidably receiving the first and second ends.

4. The apparatus of claim 1, wherein the redirection element comprises a curved wall defining an outer convex surface oriented towards a proximal end of the handle, and wherein the loop is slidably received around the convex surface such that movement of the carriage between the neutral, proximal, and distal positions causes the loop to slide around the convex surface.

5. The apparatus of claim 4, wherein the convex surface comprises HDPE to reduce friction between the loop and the curved wall.

6. The apparatus of claim 1, further comprising a tensioning element within the handle and coupled to the loop for adjusting tension on the pull wires.

7. The apparatus of claim 1, wherein the tubular member proximal end within the handle comprises a thickened wall compared to the tubular member distal end.

8. The apparatus of claim 1, further comprising a tensioning element within the handle that cooperates with one of the pull wires to adjust or apply a desired tension to one or both of the pull wires.

9. The apparatus of claim 8, wherein the tensioning element comprises a spring that applies the desired tension.

10. The apparatus of claim 8, wherein the tensioning element is configured to apply the desired tension to minimize slack.

11. The apparatus of claim 1, wherein the redirection element comprises an inner surface of a lumen of a tube in which a pull wire may be slidably received.

12. The apparatus of claim 11, wherein the tube is generally U-shaped.

13. The apparatus of claim 11, wherein the tube is comprised of a lubricious material.

14. The apparatus of claim 1, wherein the pull wires exit through the side wall openings midway through the handle.

15. The apparatus of claim 1, wherein the pull wires are coupled to subject the pull wires to axial tension in a neutral configuration, thereby applying an axial compressive force to the tubular member in the neutral configuration.

16. The apparatus of claim 1, wherein the tubular member is constructed of an elastically compressible material.

17. The apparatus of claim 1, wherein the actuator is coupled to the carriage by a screw comprising an axial passage through which the tubular member passes.

18. The apparatus of claim 17, wherein the pull wires exit the tubular member within the axial passage of the screw.

19. The apparatus of claim 1, wherein the carriage comprises an axial passage through which the tubular member passes.

20. The apparatus of claim 1, wherein the handle comprises an outer casing comprising two halves which are attached together after the internal components are assembled using one or more of cooperating connectors, bonding, and fusing.

21. The apparatus of claim 1, wherein the proximal extension is a continuation of the material of the proximal end of the tubular member.

22. A deflectable apparatus for performing a procedure within a patient's body, comprising:
  an elongate tubular member comprising a proximal end, a distal end sized for introduction into a patient's body, a central longitudinal axis extending between the proximal and distal ends, and a deflectable distal portion, and further comprising first and second auxiliary lumens spaced apart from one another on generally opposite sides of the longitudinal axis;
  a handle coupled to the proximal end of the tubular member;
  a pair of pull wires including distal ends coupled to the distal end of the tubular member and extending proximally through respective lumens of the first and second the auxiliary lumens until exiting through side wall openings in the tubular member within the handle, the pair of pull wires terminating at proximal first and second ends, respectively, that are coupled to form a loop by attachment to a carriage within the handle, one or both of the pull wires extending around a redirection element mounted within the handle, the carriage slidably disposed within the handle distal to the redirection element; and
  an actuator rotatably mounted to the handle and coupled to the carriage for directing the carriage between neutral, proximal, and distal positions within the handle, such that rotation of the actuator in a first direction with the carriage in the neutral position causes the carriage to move towards the proximal position to apply tension on the first end and deflect the distal portion in a first direction, and rotation of the actuator in a second direction opposite the first direction with the carriage in the neutral position causes the carriage to move towards the distal position to apply tension on the second end and deflect the distal portion in a second direction generally opposite the first direction,
  wherein the redirection element comprises a curved wall defining a convex surface oriented towards a proximal end of the handle, and wherein the loop is slidably received around the convex surface such that movement of the carriage between the neutral, proximal, and distal positions causes the loop to slide around the convex surface.

23. The apparatus of claim 22, wherein the curved wall is integrally molded or formed into the handle.

24. The apparatus of claim 22, wherein the convex surface comprises lubricious material to facilitate the one or both of the pull wires sliding around the convex surface.

25. A deflectable apparatus for performing a procedure within a patient's body, comprising:
  an elongate tubular member comprising a proximal end, a distal end sized for introduction into a patient's body, a central longitudinal axis extending between the proximal and distal ends, and a deflectable distal portion, and further comprising first and second auxiliary lumens spaced apart from one another on generally opposite sides of the longitudinal axis;
  a handle coupled to the proximal end of the tubular member;
  a pair of pull wires including distal ends coupled to the distal end of the tubular member and extending proximally through the respective lumens of the first and second auxiliary lumens until exiting the tubular member within the handle, the pair of pull wires terminating at proximal first and second ends, respectively, that are coupled to form a loop by attachment to a carriage within the handle, one or both of the pull wires extending around a redirection element mounted within the handle, the carriage slidably disposed within the handle distal to the redirection element; and
  an actuator rotatably mounted to the handle and coupled to the carriage for directing the carriage between neutral, proximal, and distal positions within the handle, such that rotation of the actuator in a first direction with the carriage in the neutral position causes the carriage to move towards the proximal position to apply tension on the first end and deflect the distal portion in a first direction, and rotation of the actuator in a second direction opposite the first direction with the carriage in the neutral position causes the carriage to move towards the distal position to apply tension on the second end and deflect the distal portion in a second direction generally opposite the first direction,
  wherein the pull wires are coupled to subject the pull wires to axial tension in a neutral configuration, thereby applying an axial compressive force to the tubular member in the neutral configuration.

26. The apparatus of claim 25, further comprising a tensioning element within the handle that cooperates with one of the pull wires to apply the axial tension.

* * * * *